United States Patent
Watson et al.

[11] Patent Number: 6,040,580
[45] Date of Patent: Mar. 21, 2000

[54] METHOD AND APPARATUS FOR FORMING MULTI-DIMENSIONAL ATTENUATION CORRECTION DATA IN TOMOGRAPHY APPLICATIONS

[75] Inventors: Charles C. Watson; William F. Jones, both of Knoxville, Tenn.

[73] Assignee: CTI Pet Systems, Inc., Knoxville, Tenn.

[21] Appl. No.: 09/008,848

[22] Filed: Jan. 19, 1998

Related U.S. Application Data

[63] Continuation-in-part of application No. 08/563,268, Nov. 27, 1995, Pat. No. 5,750,991, which is a continuation-in-part of application No. 08/210,960, Mar. 21, 1994, Pat. No. 5,471,061, which is a continuation-in-part of application No. 08/037,303, Mar. 26, 1993, Pat. No. 5,296,708.

[51] Int. Cl.$^7$ ..................................................... G01T 1/166
[52] U.S. Cl. .............................. 250/363.03; 250/363.04
[58] Field of Search ......................... 250/363.03, 363.04, 250/363.09, 363.1

[56] References Cited

U.S. PATENT DOCUMENTS

| | | |
|---|---|---|
| 4,743,764 | 5/1988 | Casey et al. . |
| 5,338,936 | 8/1994 | Gullberg et al. .................... 250/363.04 |

OTHER PUBLICATIONS

J.C. Moyers: "A High Performance Detector Electronics System for Positron Emmision Tomography", Masters Thesis, University of Tennessee, Knoxville, TN, 1990.

R.A. DeKemp, et al.: "Attenuation Correction in PET Using Single Photon Transmission Measurement", Med. Phys., vol. 21, 771–8, 1994.

S.R. Cherry, et al.: "3–D PET Using a Conventional Multislice Tomograph Without Septa", JI. C. A. T., 15(4) 655–668.

J.S. Karp, et al.: "Singles Transmission in vol.–Imaging PET with a 137 Cs Source", Phys. Med. Biol. vol. 40,929–944 (1955).

S.K. Yu, et al.: "Single–Photon Transmission Measurements in Positron Tomography Using 137 Cs" Phys. Med. Biol. vol. 40,1255–1266 (1955).

*Primary Examiner*—Edward P. Westin
*Assistant Examiner*—Richard Hanig
*Attorney, Agent, or Firm*—Pitts & Brittian, P.C.

[57] ABSTRACT

A method and apparatus for producing radioactive transmission measurements to form multi-dimensional attenuation correction data with a point source of radiation, such as required in positron emission tomography applications. This involves the passing of the point source proximate the face of each of the tomograph units for the formation of a 3-D image, or a selected portion of the tomograph units for a 2-D image. As such, attenuation data, transmission data, detector performance data, etc., can be obtained. This point source of radiation, in one embodiment, is rapidly circulated through a conduit that passes across each detector face under the influence of a transport fluid in, for example, an oscillatory motion to achieve a selected radiation field whereby calculation of transmission measurements within a body positioned within the tomograph scanner is achieved. When not being circulated, the radiation source is held within a shield. In another embodiment, the point source is a CT device. In a further embodiment, a single photon source is used in association with an ECAT ART having two oppositely disposed detector banks. One point source is provided for association with each detector bank. Each point source is capable of axial movement with respect to the detector banks, with the entire apparatus including the detector banks and the point sources being rotatable. Collimators are provided for each point source, the collimators and the point source being fixed with respect to each other, thus reducing the effects of dead-time during a transmission scan typically caused by the point source moving behind a collimator.

12 Claims, 9 Drawing Sheets

METHOD AND APPARATUS FOR FORMING MULTI-DIMENSIONAL ATTENUATION CORRECTION DATA IN TOMOGRAPHY APPLICATIONS

This application is a CIP of application Ser. No. 08/563,268, filed on Nov. 27, 1995, now U.S. Pat. No. 5,750,991 which is a CIP of application Ser. No. 08/210,960, filed on Mar. 21, 1994, now U.S. Pat. No. 5,471,061 which issued on Nov. 28, 1995, and which is a CIP of application Ser. No. 08/037,303 filed on Mar. 26, 1993, which issued into U.S. Pat. No. 5,296,708 on Mar. 22, 1994.

TECHNICAL FIELD

The present invention relates generally to a method and apparatus for the transmission measurement to form a multi-dimensional image for tomography applications, and more particularly to a method and apparatus for rapidly moving a point source of radiation past each detector of the tomograph apparatus together with determining the position of that source. Although described specifically for obtaining transmission attenuation in positron emission tomography, the method and apparatus is applicable for various purposes in other tomograph devices.

BACKGROUND ART

Positron Emission Tomography (PET) has gained significant popularity in nuclear medicine because of the ability to non-invasively study physiological processes within the body. PET is the most sensitive, and exhibits the greatest quantification accuracy, of any nuclear medicine imaging instrument available at the present time. Applications requiring this sensitivity and accuracy include those in the fields of oncology, cardiology and neurology.

Using compounds such as $^{11}$C-labeled glucose, $^{18}$F-labeled glucose, $^{13}$N-labeled ammonia and $^{15}$O-labeled water, PET can be used to study such physiological phenomena as blood flow, tissue viability, and in vivo brain neuron activity. Positrons emitted by these neutron deficient compounds interact with free electrons in the body area of interest, resulting in the annihilation of the positron. This annihilation yields the simultaneous emission of a pair of photons (gamma rays) approximately 180 degrees (angular) apart. A compound having the desired physiological effect is administered to the patient, and the radiation resulting from annihilation is detected by a PET tomograph. After acquiring these annihilation "event pairs" for a period of time, the isotope distribution in a cross section of the body can be reconstructed.

PET data acquisition occurs by detection of both photons emitted from the annihilation of the positron in a coincidence scheme. Due to the approximate 180 degree angle of departure from the annihilation site, the location of the two detectors registering the "event" define a chord passing through the location of the annihilation. By histogramming these lines of response (the chords), a "sinogram" is produced that may be used by a process of back-projection to produce a three dimensional image of the activity. Detection of these lines of activity is performed by a coincidence detection scheme. A valid event line is registered if both photons of an annihilation are detected within a coincidence window of time. Coincidence detection methods ensure (disregarding other second-order effects) that an event line is histogrammed only if both photons originate from the same positron annihilation.

In the traditional (2-D) acquisition of a modem PET tomograph, a collimator (usually tungsten) known as a septa is placed between the object within the field-of-view and the discrete axial rings of detectors. This septa limits the axial angle at which a gamma ray can impinge on a detector, typically limiting the number of axial rings of detectors that a given detector in a specific ring can form a coincidence with to a few rings toward the front of the tomograph from the given detector's ring, the same ring that the detector is within, and a few rings toward the rear of the tomograph from the given detector's ring. A more recent advancement in PET acquisition is 3-D, in which the septa are removed, which allows a given detector to be in coincidence with detectors from all other detector rings.

Another tomographic diagnostic system that is similar to PET is known as single photon emission computed tomography (SPECT). The distinction is that in SPECT, only a single photon from a nuclear decay within the patient is detected. Also, the line of response traveled by the photon is determined exclusively by detector collimation in SPECT, as opposed to the coincident detection of two collinear photons as in PET.

In computed axial tomography (CAT, or now also referred to as CT), an external x-ray source is caused to be passed around a patient. Detectors around the patient then respond to x-ray transmission through the patient to produce an image of an area of study. Unlike PET and SPECT, which are emission tomography techniques because they rely on detecting radiation emitted from the patient, CT is a transmission tomography technique which utilizes only a radiation source external to the patient.

The details of carrying out a PET study are given in numerous publications. Typically, the following references provide a background for PET. These are incorporated herein by reference for any of their teachings.

1. M. E. Phelps, et al.: "Positron Emission Tomography and Audiography", Raven Press, 1986;

2. R. D. Evans: "The Atomic Nucleus", Kreiger, 1955;

3. J. C. Moyers: "A High Performance Detector Electronics System for Positron Emission Tomography", Masters Thesis, University of Tennessee, Knoxville, Tenn., 1990;

4. U.S. Pat. No. 4,743,764 issued to M. E. Casey, et al, on May 10, 1988;

5. R. A. DeKemp, et al.: "Attenuation Correction in PET Using Single Photon Transmission Measurement", Med. Phys., vol. 21, 771–8, 1994;

6. S. R. Cherry, et al.: "3-D PET Using a Conventional Multislice Tomograph Without Septa", J1. C. A. T., 15(4) 655–668.

7. J. S. Karp, et al.: "Singles Transmission in Volume-Imaging PET With a $^{137}$Cs Source", Phys. Med. Biol. Vol. 40, 929–944 (1995).

8. S. K. Yu, et al.: "Single-Photon Transmission Measurements in Positron Tomography Using $^{137}$Cs", Phys. Med. Biol. Vol. 40, 1255–1266 (1995).

Both SPECT and CAT (or CT) systems are also well known to persons skilled in the art.

In order to achieve maximal quantitative measurement accuracy in tomography applications, an attenuation correction must be applied to the collected emission data. In a PET system, for example, this attenuation is dependent on both the total distance the two gamma rays must travel before striking the detector, and the density of the attenuating media in the path of travel. Depending on the location of the line of response within the patient's body, large variations in attenuating media cross section and density have to be traversed. If not corrected for, this attenuation causes unwanted spatial variations in the images that degrade the desired accuracy. As an example, for a cardiac study the attenuation is highest in the line of responses (LORs) passing through the width of the torso and arms, and attenuation is lowest in the LORs passing through from the front to the back of the chest.

Typically, the attenuation correction data in PET systems is produced by either: shape fitting and linear calculations using known attenuation constants, these being applicable to symmetric well-defined shapes such as the head and torso below the thorax (calculated attenuation); or through the measurement of the annihilation photon path's attenuation using a separate transmission scan (measured attenuation). The use of calculated attenuation correction, which introduces no statistical noise into the emission data, can be automated for simple geometries such as the head, and is the most prominent method used for brain studies. However, complexities in the attenuation media geometry within the chest have prevented the application of calculated attenuation from being practical for studies within this region of the body. Accordingly, transmission scanning has been utilized.

The total attenuation of a beam along a LOR through an object is equal to the attenuation that occurs for the two photons from an annihilation. Thus, the emission attenuation along the path can be measured by placing a source of gamma rays on the LOR outside of the body and measuring attenuation through the body along this line. It has been the practice to accomplish this attenuation measurement by placing a cylindrical positron emitter "sheet" within the PET tomograph's field of view (FOV) but outside of the region (the object) to be measured. The ratio of an already acquired blank scan (no object in the FOV) to the acquired transmission scan is calculated. These data represent the desired measured attenuation factors, which may vary spatially. These data are then applied to the emission data after a transmission scan of the object to correct for the spatial variations in attenuation.

There are two types of transmitter source units conventionally utilized in PET transmission scan data collection, both of which form a "sheet" of activity to surround the patient. One involves the placement of rings of activity aligned with detector rings around the inner face of the septa (see FIG. 1). The second type utilizes the rotation of one or more axially-oriented rods of activity in a circular path just inside the inner face of the septa (see FIG. 2).

The first of these two emitter systems (the ring source method) significantly reduces the sensitivity of the tomograph due to the close source-proximity dead time effects of the source activity on all of the detectors. Further, removal of this assembly is either performed manually by facility personnel or by a complex automated (more recent) mechanical assembly. Large, cumbersome, out of the FOV shielding is required for storage of the automated source when not in use, adding to the depth of the tomograph tunnel and, thus increasing incidence of patient claustrophobia. The second type of emitter, using rotating source(s) suffers from the above-mentioned problems and also, due to the shielding requirements, reduces the patient tunnel diameter, further increasing patient claustrophobia symptoms.

Both of the above automated source transportation methods suffer from high mechanical component cost and from low sensitivity. Due to the dead-time-induced reduction in tomograph sensitivity, lengthy acquisitions are required in order to achieve usable low noise transmission scan data.

Accordingly, it is an object of the present invention to provide a method and apparatus for rapidly moving a point source of radiation within a selected geometry to form attenuation correction data from radiation transmission measurements for correcting an emission data set, which may then be used to form an image within that geometry.

It is also an object of the present invention to provide a system that reduces the time of determining information in tomography scans.

It is another object of the present invention to provide an improved radiation emitter for carrying out attenuation data acquisition for use in obtaining increased accuracy in tomography scans.

Another object of the present invention is to provide for the controlling of a position of a point source of radiation and for determining that position so as to generate multi-dimensional attenuation correction data from radiation transmission.

It is still another object of the present invention to provide a radiation source of substantially increased activity that can be used in tomography applications.

A further object of the present invention is to provide an improved radiation emitter that requires no mechanical motion within a tomograph unit but accomplishes emission of radiation uniformly covering all detector coverage in cylindrical regions within the unit.

Another object of the present invention is to provide a method and apparatus for rapidly moving a point source of radiation within a selected geometry to form attenuation correction data from radiation transmission measurements for correcting an emission data set, wherein the point source of radiation is a CT scanner.

It is also an object of the present invention to provide a method and apparatus for using a single photon source having associated collimators to illuminate opposing, non-collimated, detectors.

These and other objects of the present invention will become apparent upon a consideration of the drawings forming a part of the disclosure of the invention, together with a complete description thereof that follows.

DISCLOSURE OF THE INVENTION

In accordance with the present invention, there is provided a method and apparatus for causing a point source of radiation to rapidly move in a selected path around or adjacent to an object being subjected to a tomography scan to generate multi-dimensional attenuation correction data from radiation transmission through that selected path. This system utilizes substantially no moving components within the region of the object and thus substantially reduces cost associated with obtaining transmission data. The system utilizes a point source which may be carried within a tubing placed adjacent the surface of radiation detector faces such that the point source is passed adjacent each detector face or which may be a CT device carried on a single rotational support with the PET or SPECT device. In the first instance, the point source of a selected shape, which typically can be a sphere or a small cylinder, and is carried within a transport fluid typically moved by a positive displacement pump from a shielded position, through the tubing a selected number of times, and then returned to a storage shield. Typically the source is repetitively passed in an oscillatory manner through the tubing. Thus, the origination of the radiation from the point source can be controlled so as to direct radiation across the tomograph apparatus volume and through the object, with the conventional detectors being used to determine transmission data. In one embodiment of the invention for use in PET systems, the tubing is formed into a cylindrical helix and the transmission data is used to obtain photon attenuation data. In an alternate embodiment, the tubing is formed into a substantially linear configuration such that the point source is moved in a direction substantially parallel to the longitudinal axis of the tomograph apparatus. In the embodiment wherein the point source is a CT device, the tomograph device includes two banks of detectors on opposite sides of a ring. Gaps are defined between the banks of emission tomograph detectors. In one gap is positioned a bank of CT detectors. An X-ray generator is positioned to generate X-rays and direct the same through the opposing gap and the patient toward the bank of X-ray detectors. The CT device and detectors are stationary with respect to the emission tomograph device such that both the emission tomograph device and the CT device simultaneously acquire data.

In a further embodiment, a single photon source such as $^{137}Cs$ (662 keV) is used in association with an Emission Computerized Axial Tomography Advanced Rotating Tomograph (ECAT ART), wherein two oppositely disposed detector banks are rotated about the subject being studied. Alternatively, a positron emitting source such as $^{68}Ge/^{68}Ga$ may be used in a non-coincidence (singles) mode of operation. In this embodiment of the present invention, one point source is provided for association with each detector bank. Each point source is capable of axial movement (parallel to the axis of the ART) with respect to the detector banks, with the entire apparatus including the detector banks and the point sources being rotatable. Thus, while the point source is oscillating in an axial direction and the ECAT ART is rotating, the travel of the point source follows a substantially helical path. Collimators are provided in association with each point source, the collimators being configured such that each terminates a distance from the axis of the ART substantially equal to the radius of each detector bank, thus providing a single photon source while not reducing the volume within the ART. While collimation reduces the usable count rate for a singles source by a factor of approximately three, the scatter fraction is also reduced.

BEST MODE FOR CARRYING OUT THE INVENTION

As discussed hereinafter, the present invention is applicable to producing multi-dimensional attenuation correction data from radiation transmission measurements for correcting an emission data set, which may be used to form an image within that geometry. It is especially applicable for many types of tomography applications, such as with PET, SPECT, or ECAT ART. The invention is described, for purposes of illustration, for an ECAT ART unit.

Figure 1:
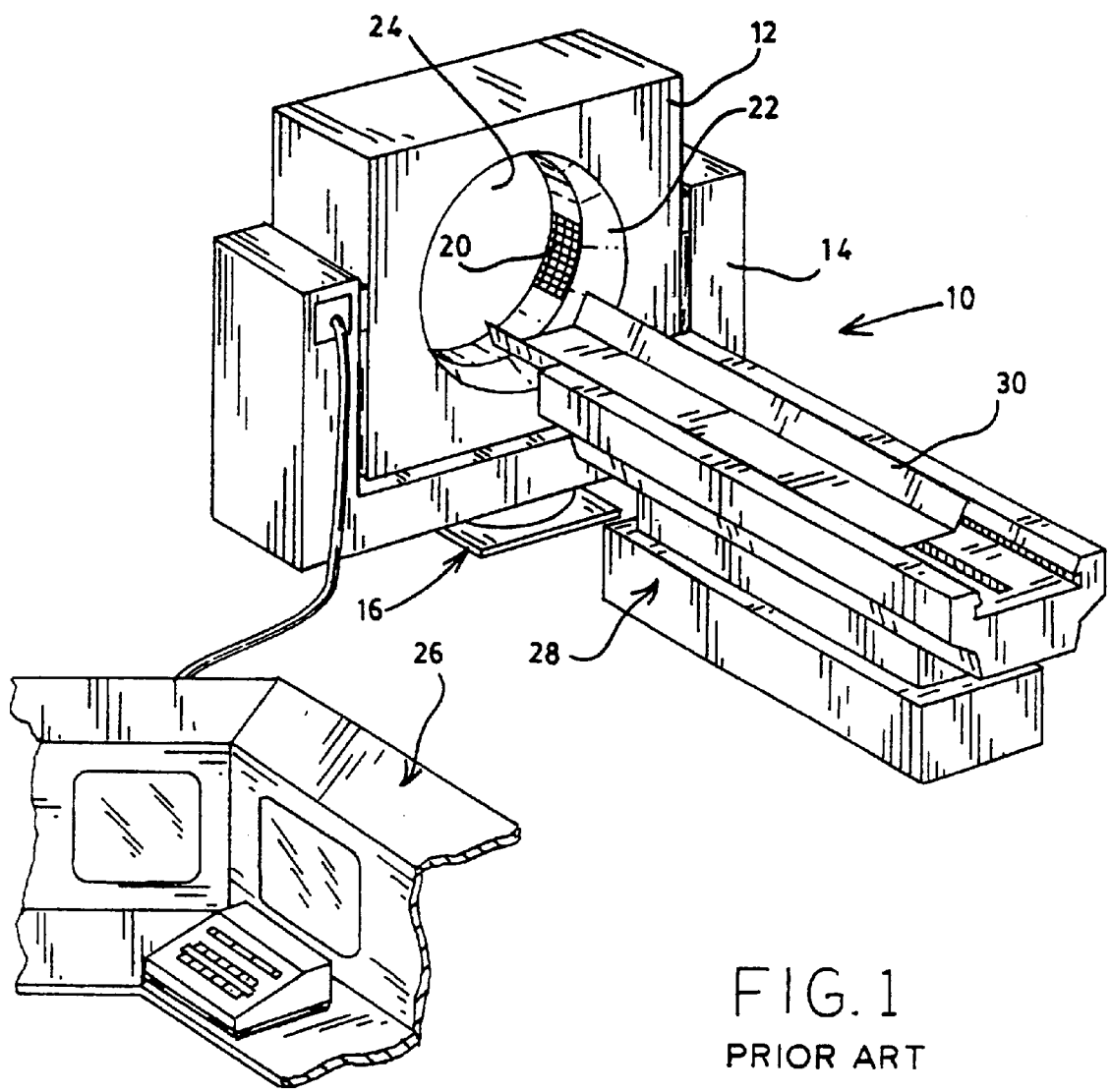
FIG. 1 is an isometric drawing illustrating a typical tomograph unit for a better understanding of the present invention.

For an understanding of a tomograph unit, reference is made to FIG. 1 where such unit is indicated generally at 10. In general, this unit 10 includes a gantry 12 of conventional design mounted upon a U-shaped mounting bracket 14 supported on a base 16. Detectors 20 for diagnostic imaging operations are carried in a cylindrical array on a ring 22, with the faces of the detectors 20 forming a cylindrical opening 24 for receiving a selected portion of a patient's body. Signal outputs from the detectors 20 are carried to a monitoring station 26 for analysis and display in a typical manner. This station 26 contains processing means for producing attenuation correction data and for combining this attenuation correction data with normal scan data from the unit. The unit includes a patient bed 28, which includes a sliding carriage 30, for moving the selected body portion into and out of the opening 24 in a conventional manner.

Figure 2:
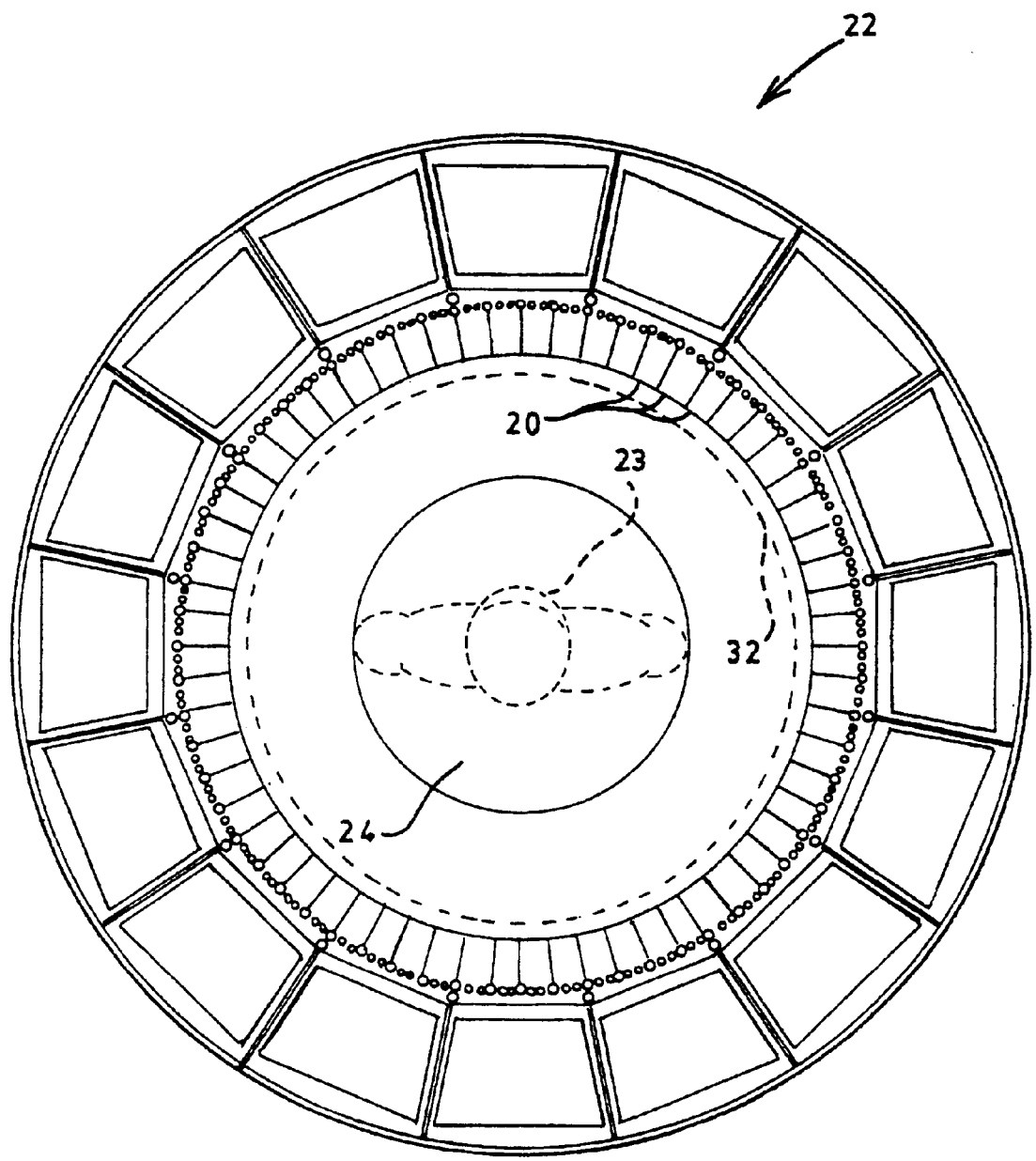
FIG. 2 is a cross-sectional view of a typical PET tomograph unit illustrating placement of detectors relative to an object, together with the placement of the point source of the present invention in the PET unit embodiment.
Figure 4:
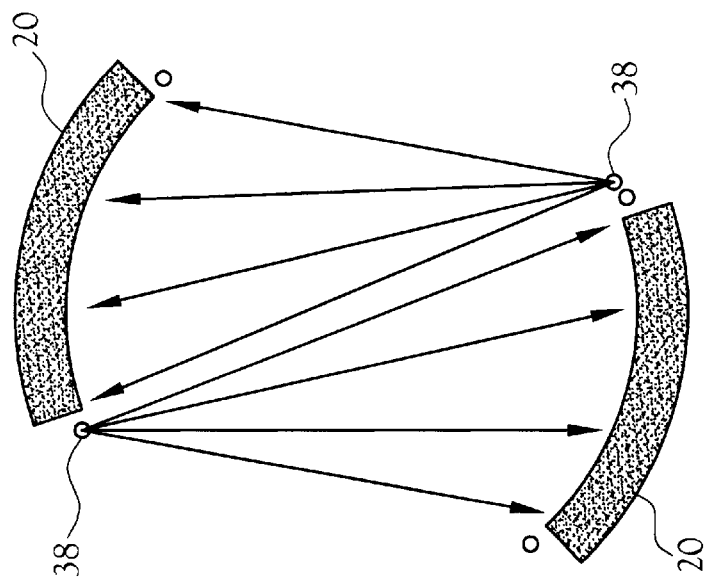
FIG. 4 illustrates the disposition of two single photon point sources with respect to two detector banks comprising the ECAT ART of FIG. 3.

FIG. 2 is a cross-sectional view of the aforementioned ring 22 with the detector units 20 mounted thereon. This figure illustrates the position of a patient 23 as located on a central axis of the cylindrical array of detectors 20. This geometric arrangement is such as to generate the positron radiation from within the patient to impinge upon the various detectors 20 for achieving scan data.

In the inventions previously disclosed in patent application Ser. No. 08/563,268, filed on Nov. 27, 1995, and in U.S. Pat. Nos. 5,471,061, issued on Nov. 28, 1995, and 5,296,708, issued on Mar. 22, 1994, a point source is hydraulically manipulated through a tubing for rastering the point source in front of each detector. The point source may be rastered through a helically-configured tube, or a linear tube. Further, the detectors may be collimated or uncollimated. In the former case, the point source is passed between the detectors and the collimators, or septa. The disclosure of each of these inventions is incorporated herein by reference.

In the present invention, which is a derivative of those embodiments disclosed and incorporated herein by reference, a single point source 38 is associated with at least one point source collimator 74, with the detectors 20 remaining uncollimated. As in the previously disclosed embodiments, the point source 38 of radiation (e.g., gamma rays) can be, for example, either a small sphere or a small cylinder. One material used to fabricate the source 38 is $^{68}$Ge encapsulated in a gold enclosure which produces positrons like those that are emitted during the annihilation within the patient's body. Since gold is rather easily abraded, an outer hard coating of plastic or other low attenuation material is usually applied over the gold layer. In a further embodiment, the point source 38 of radiation is a CT device mounted on a single rotational support within the tomography device 10. Specifically, a bank of CT detectors is placed within a gap defined between two banks of detector units 20. A CT generator (X-ray generator) is positioned on the opposite side of the ring 22 to direct X-rays through the patient 23 to the bank of CT detectors. The CT device is moved about the patient 23 in a conventional fashion along with the detector banks 20 and attenuation correction data is collected as in the previously described embodiments. However, CT scanning devices provide correction factors at lower energies (i.e., 40–120 keV as compared to 511 keV) than those desired. In order to accommodate for correction factors obtained from the CT scan, the correction factors obtained from the CT scan are scaled to achieve the appropriate value. Any of several scaling methods may be used in order to accomplish this task. Some of the scaling methods are: (1) simple global scaling based on the ratio of attenuation for water at the two energies (the obtained energy level and the desired energy level); (2) implementation of a CT device having dual energy capability, whereby scaling is actually unnecessary; (3) segmentation of the reconstructed CT image obtained from the scan into different regions such as tissue, bone and lungs, and using appropriate attenuation coefficients to scale data in each region; and (4) a hybrid of methods (1) and (3) above. For method (3), an exemplary scale factor is approximately 2.26 for bone regions and 1.85 for non-bone regions.

It will be understood that any other conventional device for obtaining anatomical data may be used in lieu of the CT scanner as described, as any other conventional device for obtaining functional data may be used in lieu of those discussed. Because the devices are mounted on a common rotational support, anatomical and functional data sets obtained therefrom are closely aligned. Therefore, registration of the two data sets is accommodated, while eliminating problems which arise when the two scans are performed using two separate scanners.

Figure 3:
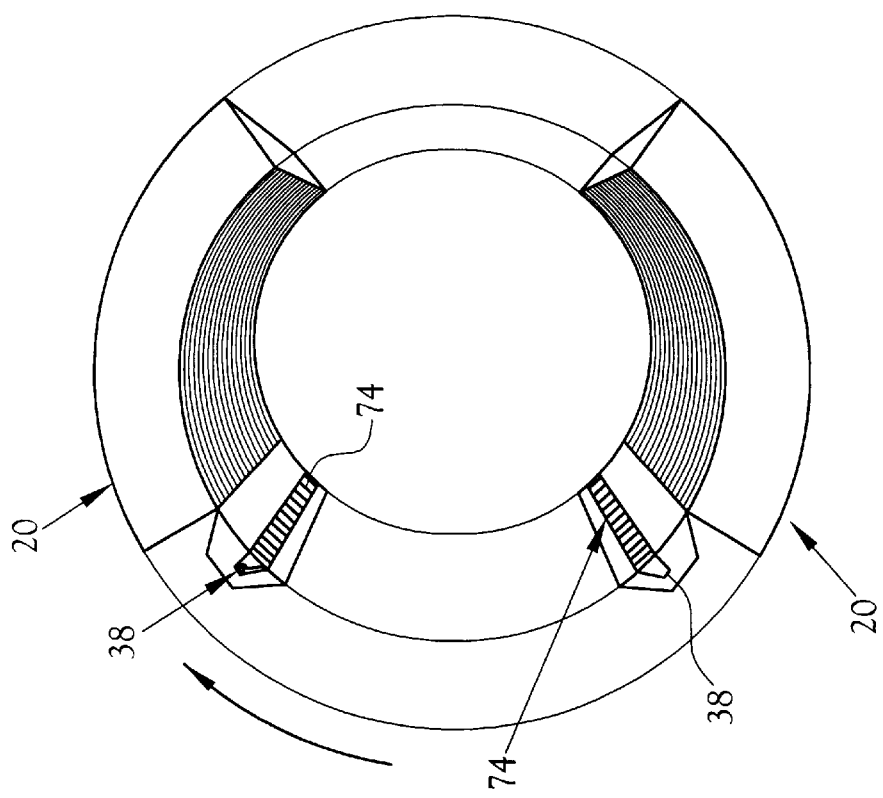
FIG. 3 illustrates an alternate embodiment of the present invention used in association with an ECAT ART.

In the embodiment illustrated in FIG. 3, a single photon source 38 such as $^{137}$Cs (662 keV) is used in association with an ECAT ART. Alternatively, a positron emitting source such as $^{68}$Ge/$^{68}$Ga may be used in a non-coincidence detector (singles) mode of operation. In an ART, two oppositely disposed detector banks 20 are rotated about the subject being studied. In the illustrated embodiment of the present invention, one point source 38 is provided for association with each detector bank 20. Each point source 38 is capable of axial movement (parallel to the axis of the ART) with respect to the detector banks 20, with the entire apparatus including the detector banks 20 and the point sources 38 being rotatable. Thus, while the point source 38 is oscillating in an axial direction and the ECAT ART is rotating, the travel of the point source 38 follows a substantially helical path.

Collimators 74 are provided in association with each point source 38. The collimators 74 are configured such that each terminates a distance from the axis of the ART substantially equal to the radius of each detector bank 20, thus providing a single photon source 38 while not reducing the volume within the ART. While collimation reduces the usable count rate for a singles source by a factor of approximately three, the scatter fraction is also reduced. For example, in a 20 cm phantom, the scatter fraction is reduced from approximately twenty-one percent (21%) to approximately six percent (6%).

Figure 5:
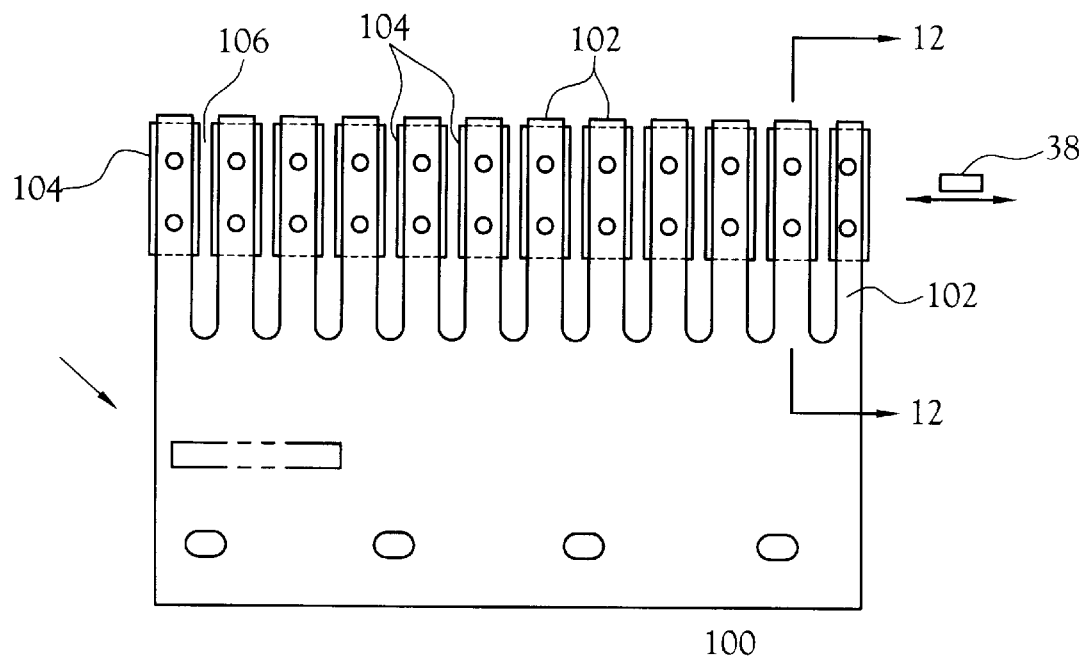
FIG. 5 is a front elevation view of a collimator used in association with the embodiment of the present invention of FIG. 3.
Figure 6:
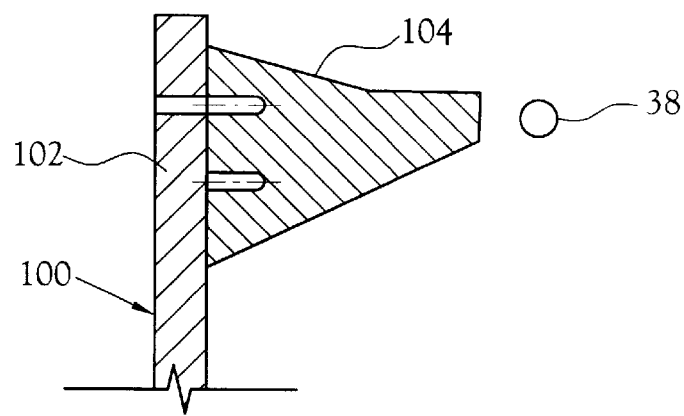
FIG. 6 is a side elevation view of the collimator of FIG. 5.

In this example, each set of collimators 74 includes twelve slits 106 having an aperture ratio of 15:1 (depth:width) and an axial pitch of twice the axial crystal ring pitch, the crystal rings combining to form a detector bank 20. Each slit 106 is defined between two collimator wedges 104 as illustrated in FIG. 5, the collimator wedges 104 being carried on a collimator finger 102 defined by a collimator base 100. Each collimator wedge 104 in this embodiment defines a profile as illustrated in FIG. 6. The collimator wedges 104 of the preferred embodiment are fabricated from machinable tungsten, while the collimator base 100 is preferably fabricated from 6061-T6 aluminum. The point source 38 is rastered proximate the distal ends of the collimator wedges 104, thus yielding a photon emission through successive slits 106. The slits 106 illuminating opposing detector banks 20 are interleaved in order to achieve fill coverage of all crystal rings.

Figure 7:
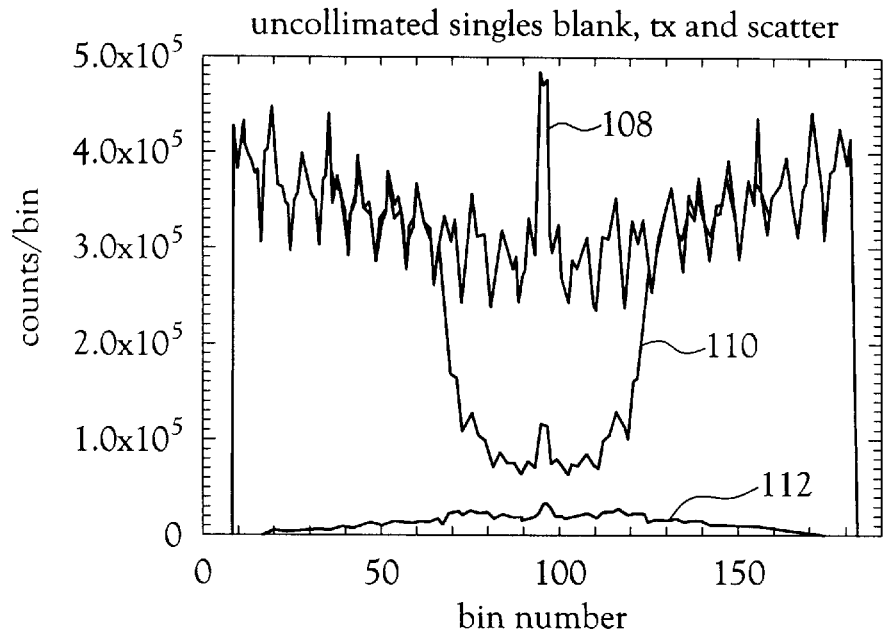
FIG. 7 is a graph illustrating the transverse profiles of an uncollimated point source, showing a blank scan, a transmission scan, and estimated scatter.

Several tests have been performed to determine the benefit of the collimated point source 38, one such test including two sets of $^{137}$Cs singles blank and transmission scans on a centered 20 cm water phantom. The scans were performed under identical conditions, with the exception of the presence of a collimator 74 in one scan. A single 6 mCi point source 38 was contained in a shielding block adjacent to the last detector 20 on the short side of one detector bank 20. The source 38 was placed behind an axial collimator 74 whose aperture width was 2 mm and depth was 30 mm, yielding a transverse fan beam. A 15 minute blank and a 30 minute transmission were acquired, the axial collimator 74 was removed, and the scans were repeated. The LLD was 500 keV and the ULD was 800 keV. FIG. 7 illustrates the transverse profiles through the blank and transmission sinograms 108,110, along with the estimated scatter 112, for the uncollimated case. The high frequency structure is due to detector efficiency variations as a result of the fixed position of the point sources 38 relative to the detectors 20. For a simple water cylinder being used as the object under test, a true attenuation profile ($e^{-\mu l(r,z)}$) is readily computed. The scatter in the transmission data is estimated from:

$$\text{scatter}^{est} = tx_{meas} - \text{blank}_{meas} e^{-\mu l(r,z)}.$$

Without collimation as described in this embodiment, the estimated scatter is approximately twenty-one percent (21%), whereas in the collimated case as described, the estimated scatter is approximately six percent (6%). Thus, the estimated scatter is reduced by approximately two-thirds.

Figure 8:
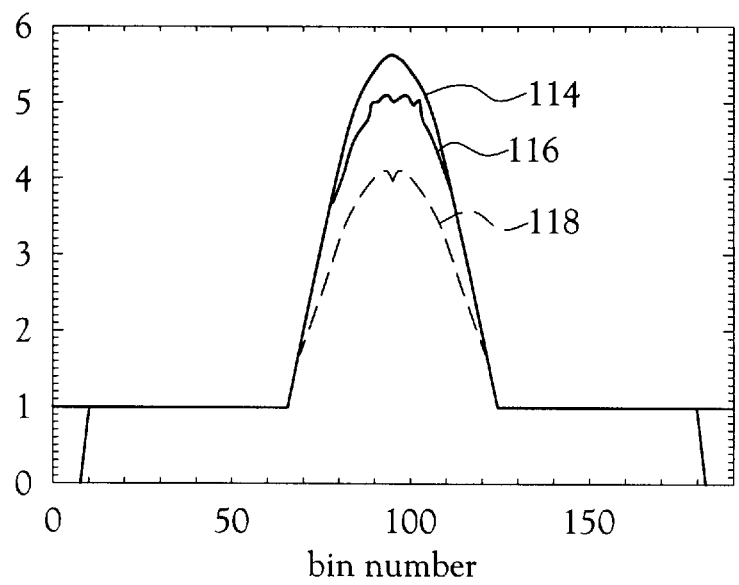
FIG. 8 is a graph illustrating the transverse profiles of uncompensated attenuation correction factors contrasting a model profile, collimated singles data, and uncollimated singles data.

FIG. 8 illustrates the transverse profiles of uncompensated attenuation correction factors for the water phantom. The top curve 114 is the model profile, the middle curve 116 is from the collimated singles data, and the bottom curve 118 from the uncollimated measurement. It can clearly be seen that systematic error in the collimated singles data is greatly reduced in comparison to the uncollimated singles data.

It is standard practice to compute attenuation correction factors from a transmission sinogram by taking its ratio to a blank scan, a technique which is well known to those skilled in the art. This technique can also be applied to the singles point source data. However, to provide for more exact cancellation of detector efficiency variations, it can be beneficial to normalize the transmission sinogram to a slab phantom scan instead of a blank. Thus, a uniformly attenuating medium such as a uniform rectangular block of plastic, or a water-filled box, approximately 15 cm thick and extending across the axial and transverse fields of view is centered in the gantry and scanned. Data acquired at projection angles nearly normal to the surface of the block are averaged to form a radial profile analogous to the rows of a blank sinogram. Because the attenuation coefficient of the reference phantom is known, it is straightforward to account for such in the computation of the attenuation factors.

Measured attenuation factors are compensated for object scatter on the approximation that its main effect is to stretch the attenuation path length. This leads to a multiplicative correction of the linear attenuation coefficients. The ratio of the linear attenuation coefficients of 511 keV photons and 662 keV photons is biological materials is nearly constant and hence the difference in photon energy between the $^{137}$Cs transmission data and the positron annihilation radiation data can also be compensated by a simple scaling. Thus, the logarithm of the desired attenuation correction factors (ACF) at 511 keV are estimated from:

$$\ln(ACF)=a+b\ \ln(\text{slab}/tx),$$

where a and b are constants.

Figure 9:
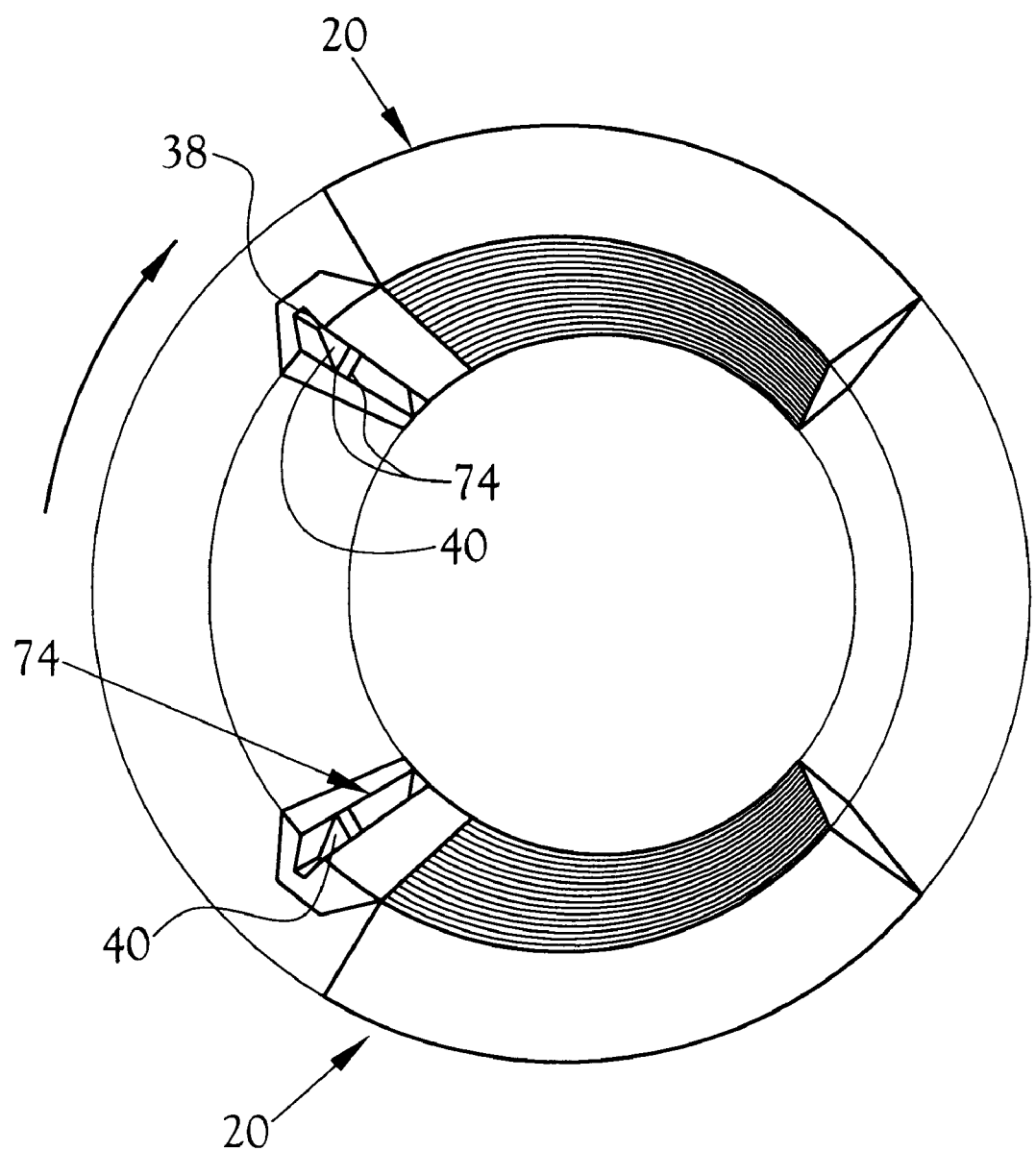
FIG. 9 illustrates an alternate embodiment of the present invention used in association with an ECAT ART, wherein the collimators associated with the point source are fixed relative to the point source, and wherein the point source and collimators are rastered in an axial direction.

In a further alternate embodiment, illustrated in FIG. 9, a point source housing 40 is provided with a collimator 74 defining a single slit 76. A point source 38 is positioned within the housing in alignment with the single slit 76. In this embodiment, the point source housing 40 is rastered in an axial direction in order to perform the attenuation functions previously described. By moving the collimator 74 with the point source 38, several benefits are achieved. Namely, the mechanism required for moving the point source 38 is simple as compared to mechanisms for moving only the point source 38. Also, there is no dead time as a result of the point source 38 being passed behind a collimator wedge 104 as before.

Figure 10:
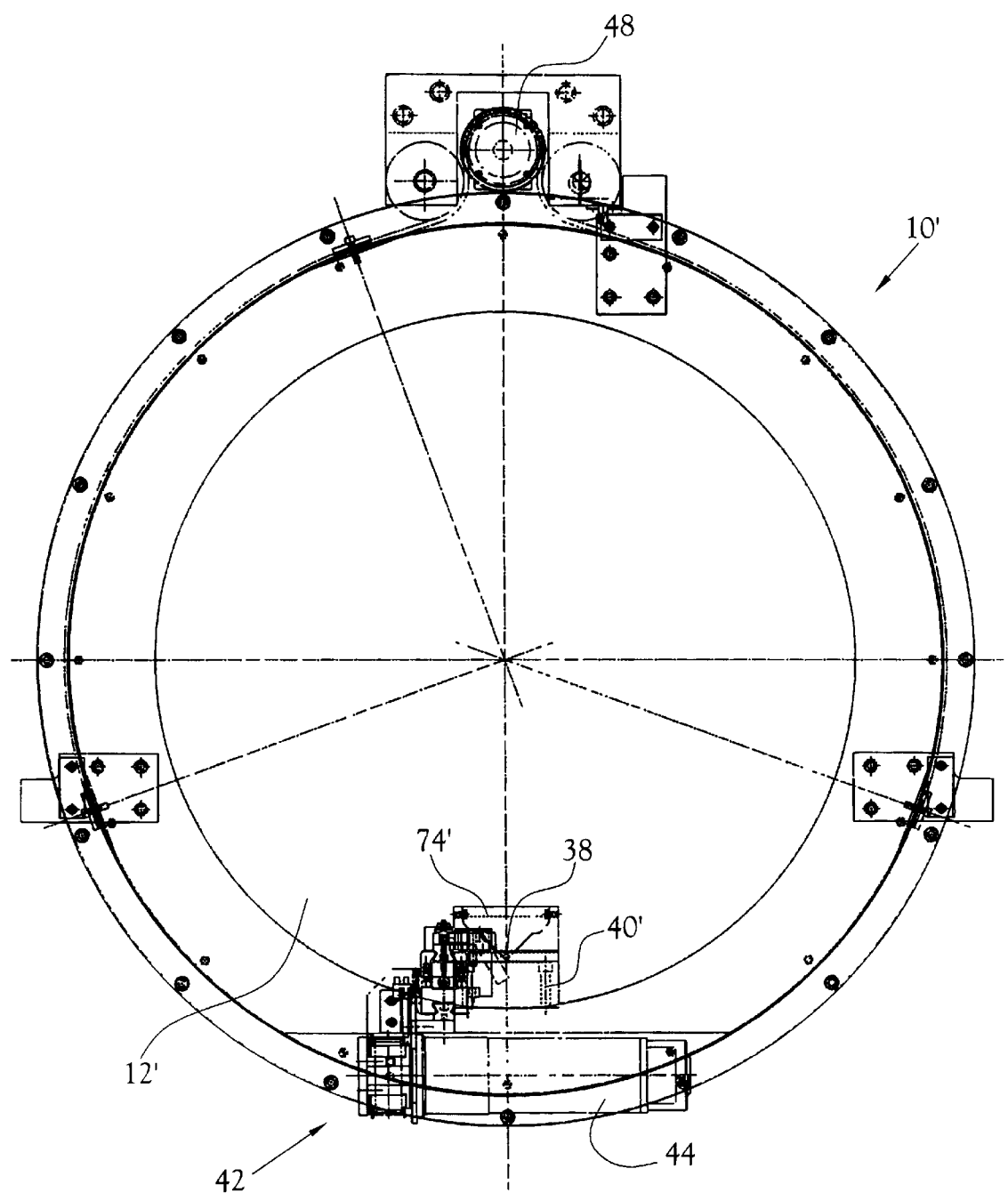
FIG. 10 illustrates an end view of an alternate embodiment of the present invention wherein the point source is received within a housing having a single slit collimator, the housing being rastered in an axial direction and rotated about the tomograph to accomplish positioning the point source in front of any detector face.
Figure 11:
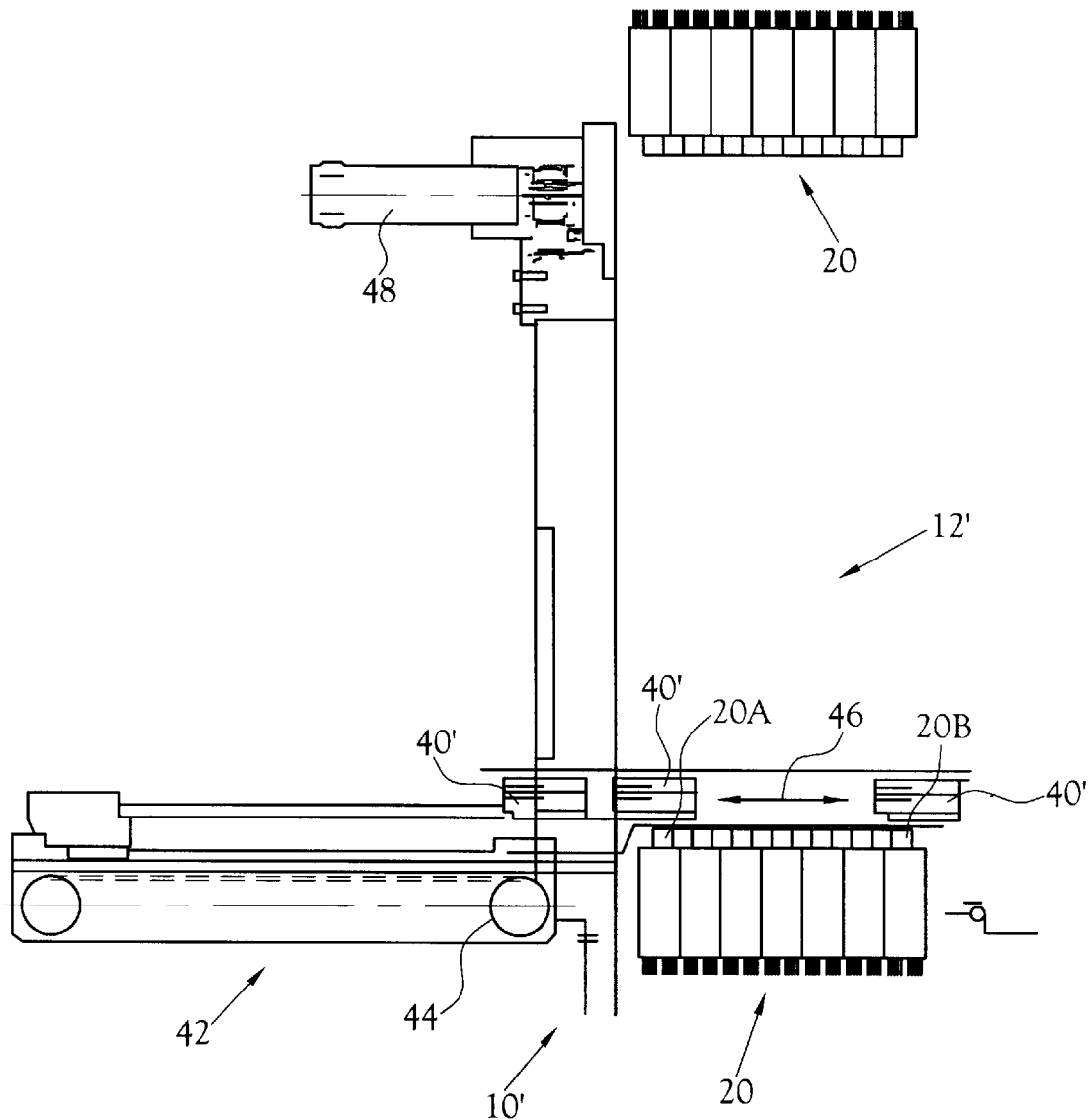
FIG. 11 illustrates a side elevation view of the alternate embodiment of FIG. 10 illustrating the point source housing in a parked position and in two extended positions within the tomograph.
Figure 12:
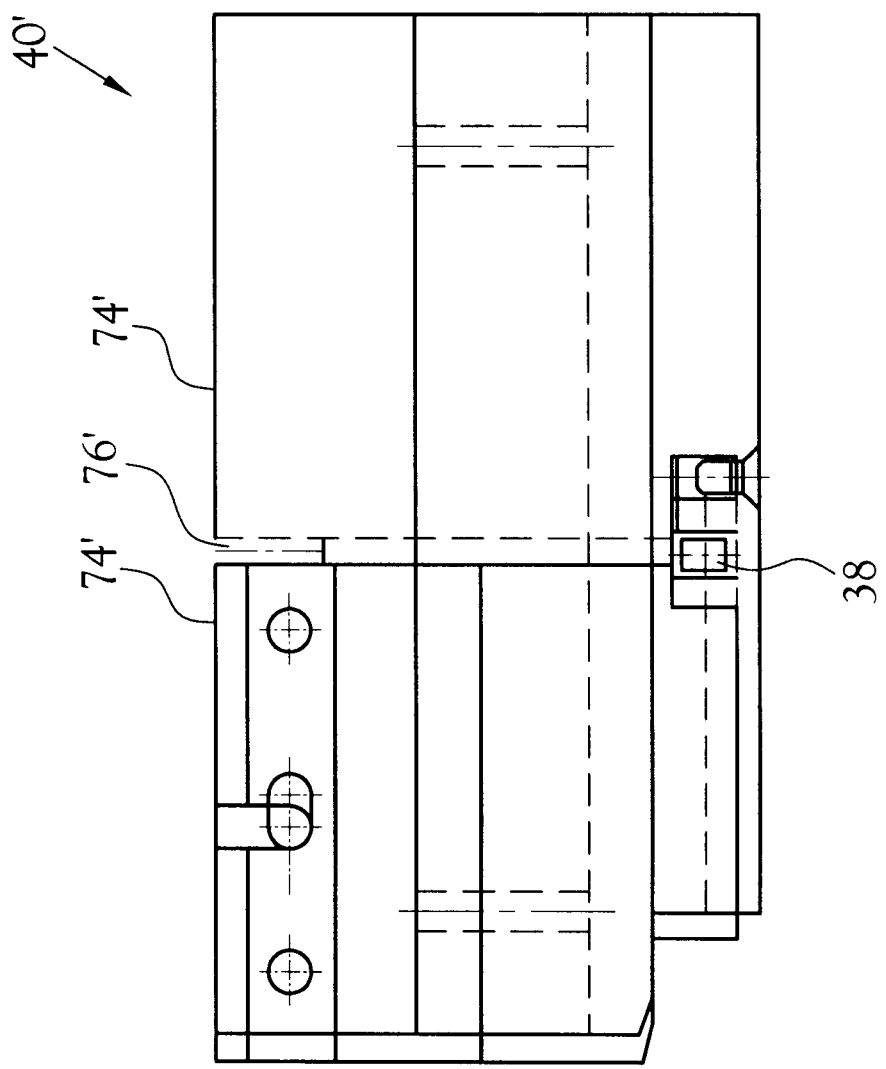
FIG. 12 illustrates a side elevation view of the point source housing of FIG. 10.

Another alternate embodiment illustrated in FIGS. 10–12, is used in association with a High Resolution Research Tomograph (HRRT) 10' which utilizes a stationary bank of detectors 20. A single point source 38 is disposed within a point source housing 40' in alignment with a collimator slit 76'. The point source housing 40' is rastered axially as indicated at 46 in FIG. 11.

The point source housing 40' is carried by a point source carrier assembly 42 including two motors 44,48. An axial motion motor 44 is provided for rastering the point source housing 40' as described above. A rotational motion motor 48 is provided for moving the point source carrier assembly 42 in an arcuate path along the radius of the bank of detectors 20. In the preferred embodiment, the point source housing 40' is rastered along one row of detectors 20 using the axial motion motor 44. FIG. 11 illustrates the axial motion motor 44 in a parked position, with the point source carrier assembly 42 being retracted from the tomograph gantry 12'. Also illustrated is the point source housing 40' positioned above the first and last detectors 20A,B in one row of detectors 20, thus illustrating the extent of travel of the point source carrier assembly 42 in an axial direction.

FIG. 12 more clearly illustrates the point source housing 40' of FIGS. 10 and 11. The point source housing 40' defines a single collimator slit 76' through which radiation is emitted from the point source 38. To this extent, the point source 38 is carried within the point source housing 40' coincident with the collimator slit 76'.

The rotational motion motor 48 is provided for moving the point source carrier assembly 42 between rows of detectors 20. The point source housing 40' is then rastered along the subsequent row of detectors 20. This process is repeated through a selected portion of the detector bank 20. In the preferred embodiment, the rotational motion motor 48 is capable of moving the point source carrier assembly 42 through at least one hundred eighty degrees (180°) of the detector bank 20. In the illustrated embodiment, the rotational motion motor 48 is capable of moving the point source carrier assembly 42 through approximately three hundred sixty degrees (360°).

The goal of this process is to obtain a density map in order to test a particular line of response. Thus, it has been found that a scan of the entire bank or banks of detectors 20 is not required. This is especially true in those tomographs 10 which do not define a continuous detector ring 22 such as the ECAT ART. However, it will be noted that as the number of lines of response tested increases, the efficiency of the density map will likewise increase.

It is known in the art that a patient must lie motionless during and between the transmission and emission scans in order to achieve accurate results. Due to this requirement and the time required for tracer uptake in the body before emission scanning can commence, it is often impractical to carry out the transmission scan before the patient is injected with a radiopharmaceutical. It is therefore frequently necessary to carry out the transmission scan post injection, while the patient is emitting radiation. This emitted radiation can only be partially discriminated against during the collection of transmission data. The residual emitted radiation contaminates the transmission data and can lead to errors in its interpretation. In order to correct for the residual radiation, one of two methods may be employed.

In one method, a mock transmission scan is used to measure the emission background in the actual transmission scan. A mock transmission scan is accomplished by configuring the scanner to accept singles data as described above for an actual transmission scan, with the exception that the transmission sources are not exposed. Thus, only background counts from the patient are collected. After possibly correcting these data for dead time, they are subtracted from the actual transmission scan data, resulting in a corrected transmission scan. This method is similar to a mock scan technique proposed for rod-windowed coincidence transmission measurements by R. J. Smith, et al., *IEEE Trans. Nucl. Sci.*, vol. 41, pp. 1526–1531, 1994.

In an alternate method, the mock scan is not required. This is due to the fact that emission background is collectable in an emission scan. Each event detected during an emission scan which is in coincidence with another event within a defined field of view is normally histogramed into the emission sinogram. However, each such event, it if is determined to be of the appropriate energy, could also be histogramed as if it had been collected during a mock scan, as described above. Since the assumed position of the transmission sources during a mock scan is entirely arbitrary, all events of the appropriate energy collected during the emission scan can contribute to the mock data set, and in fact to multiple bins of the sinogram, greatly enhancing the efficiency of this method. As in the previously described method, the background sinogram acquired in this way is possibly corrected for dead-time and then subtracted from the actual transmission scan data, resulting in a corrected transmission scan.

From the foregoing, it will be understood by persons skilled in the art that an improvement has been made to the manner of determining attenuation data in a tomograph unit. Further, while providing data from attenuation through a body for tomograph scanning, the system can also be used to determine the overall response of the radiation detectors of the basic tomograph system.

The present invention has been described in detail as applied to positron emission tomograph (PET) units, ECAT ART units, and/or High Resolution Research Tomograph (HRRT) units for illustration purposes. Due to the ability of the method and apparatus to rapidly move a point source of radiation in a selected 2-D or 3-D geometry, and to determine the position of that source, the present invention is applicable to various tomography applications. Further, the present invention is applicable for producing 2-D and 3-D transmission measurement images in any selected geometry and for any desired utilization of such images.

Although certain specific materials are recited herein, these are for illustrative purposes and not for limiting the invention. Accordingly, the invention is to be limited only by the appended claims and equivalents thereof when read together with the complete description of the present invention.

We claim:

1. A method for forming at least one of a multi-dimensional attenuation data set and an image of radiation transmission through an object positioned in a tomograph device, said tomograph device being at least one of a positron emission tomography (PET) device, a single photon emission computed tomography (SPECT) device and an ECAT ART device, said tomograph device having radiation detectors defining a plurality of faces, said tomograph device including a plurality of collimators, said method comprising the steps of:

positioning at least one selected point source of radioactive radiation proximate at least one of said plurality of collimators in a selected sequence, said radioactive radiation being directed through the object and received by a selected subset of said radiation detectors of said tomograph device; and processing signals received from outputs of said detectors of said tomograph device to determine transmission data from radiation from said source of radiation during passage of said radiation through the object for forming said at least one of an attenuation data set and an image.

2. The method of claim 1 further comprising detecting the location of said source of radiation.

3. A system for forming at least one of a multi-dimensional attenuation data set and an image of radiation transmission through an object positioned in a tomograph device, said tomograph device being at least one of a positron emission tomography (PET) device, a single photon emission computed tomography (SPECT) device and an ECAT ART device, said tomograph device having radiation detectors defining a plurality of faces of said radiation detectors, said system comprising:

at least one selected point source of radioactive radiation, said radiation directed through the object and received by a selected subset of said detectors of said tomograph device;

at least one point source carrying assembly for receiving said point source and for moving said point source in front of said radiation detectors;

signal processing circuitry connected to outputs of said detectors of said tomograph device to determine transmission data from radiation from said source of radiation during passage of said radiation through the object; and at least two collimators positioned over said at least one point source, said at least two collimators being adapted to define at least one collimator slit through which radiation is emitted from said at least one point source to said selected subset of said detectors.

4. The system of claim 3 further comprising further processing circuitry connected to said outputs of said selected subset of said detectors of said tomograph device and to said signal processing circuitry to apply said transmission data of said radiation source to data from annihilation photon emission from within the object to said detectors of said tomograph device.

5. The system of claim 3 wherein said tomograph device is an ECAT ART device including a first detector bank and a second detector bank, and wherein said plurality of collimators includes a first set of collimators positioned proximate said first detector bank and a second set of collimators positioned proximate said second detector bank, and wherein said at least one point source includes a first point source positioned behind said first set of collimators to illuminate a selected subset of said second detector bank and a second point source positioned behind said second set of collimators to illuminate a selected subset of said first detector bank, each of said first and second point sources being limited to axial travel behind said first and second sets of collimators, respectively.

6. The system of claim 3 wherein said point source carrying assembly includes a point source housing, said point source housing being provided for receiving said point source and for carrying said at least two collimators, said at least two collimators including a first collimator and a second collimator, said at least one collimator slit including a first collimator slit, said point source being fixed relative to said first and second collimators and positioned within said point source housing such that said radiation is emitted through said first collimator slit, said point source carrying assembly being provided for rastering said point source housing in an axial direction with respect to said tomograph device.

7. The system of claim 6 wherein said point source carrying assembly includes an axial motion imparting device and a rotational motion imparting device, said axial motion imparting device for rastering said point source housing in an axial direction, said rotational imparting device being provided for rotating said point source housing about said tomograph device in an arcuate manner, said point source carrying assembly thereby being provided for moving said point source to a point proximate any of said tomograph device radiation detectors.

8. A system for forming at least one of a multi-dimensional attenuation data set and an image of radiation transmission through an object positioned in a tomograph device, said tomograph device being an ECAT ART device including a first detector bank and a second detector bank, each of the first and second detector banks having radiation detectors defining a plurality of faces of said radiation detectors, said system comprising:

at least one selected point source of radioactive radiation, said radiation directed through the object and received by said detectors of said tomograph device;

at least one point source carrying assembly for receiving said point source and for moving said point source in front of said radiation detectors;

signal processing circuitry connected to outputs of said detectors of said tomograph device to determine transmission data from radiation from said source of radiation during passage of said radiation through the object; and at least two collimators positioned over said at least one point source, said at least two collimators cooperating to define at least one collimator slit through which radiation from said at least one point source is emitted, wherein said at least two collimators includes a first set of collimators positioned proximate said first detector bank and a second set of collimators positioned proximate said second detector bank, and wherein said at least one point source includes a first point source positioned behind said first set of collimators to illuminate said second detector bank and a second point source positioned behind said second set of collimators to illuminate said first detector bank, each of said first and second point sources being limited to axial travel behind said first and second sets of collimators, respectively.

9. The system of claim 8 further comprising further processing circuitry connected to said outputs of said detectors of said tomograph device and to said signal processing circuitry to apply said transmission data of said radiation source to data from annihilation photon emission from within the object to said detectors of said tomograph device.

10. A system for forming at least one of a multidimensional attenuation data set and an image of radiation transmission through an object positioned in a tomograph device, said tomograph device being at least one of a positron emission tomography (PET) device, a single photon emission computed tomography (SPECT) device and an ECAT ART device, said tomograph device having radiation detectors defining a plurality of faces of said radiation detectors, said system comprising:

at least one selected point source of radioactive radiation, said radiation directed through the object and received by said detectors of said tomograph device;

at least one point source carrying assembly for receiving said point source and for moving said point source in front of said radiation detectors, said point source carrying assembly including a point source housing for receiving said point source;

signal processing circuitry connected to outputs of said detectors of said tomograph device to determine transmission data from radiation from said source of radiation during passage of said radiation through the object; and first and second collimators carried by said point source housing and positioned over said at least one point source, said first and second collimators cooperating to define at least one collimator slit through which radiation from said at least one point source is emitted, said at least one collimator slit including a first collimator slit, said point source being fixed relative to said first and second collimators and positioned within said point source housing such that said radiation is emitted through said first collimator slit, said point source carrying assembly being provided for rastering said point source housing in an axial direction with respect to said tomograph device.

11. The system of claim 10 wherein said point source carrying assembly includes an axial motion imparting device and a rotational motion imparting device, said axial motion imparting device for rastering said point source housing in an axial direction, said rotational imparting device being provided for rotating said point source housing about said tomograph device in an arcuate manner, said point source carrying assembly thereby being provided for moving said point source to a point proximate any of said tomograph device radiation detectors.

12. The system of claim 10 further comprising further processing circuitry connected to said outputs of said detectors of said tomograph device and to said signal processing circuitry to apply said transmission data of said radiation source to data from annihilation photon emission from within the object to said detectors of said tomograph device.

* * * * *